United States Patent [19]

Iijima et al.

[11] Patent Number: 4,948,900

[45] Date of Patent: Aug. 14, 1990

[54] BENZOXAZOLE DERIVATIVES

[75] Inventors: Ikuo Iijima, Urawa; Masakatsu Ozeki, Wako; Kunihito Okumura, Urawa; Masanori Inamasu, Misato, all of Japan

[73] Assignee: Tanabe Seiyaku Co., Ltd., Osaka, Japan

[21] Appl. No.: 435,807

[22] Filed: Nov. 13, 1989

Related U.S. Application Data

[62] Division of Ser. No. 167,391, Mar. 14, 1988, Pat. No. 4,897,393.

[30] Foreign Application Priority Data

Mar. 18, 1987 [JP] Japan .................................. 62-65359
Mar. 20, 1987 [JP] Japan .................................. 62-67073

[51] Int. Cl.$^5$ ............................................ C07D 277/34
[52] U.S. Cl. ...................................... 548/183; 548/181
[58] Field of Search ......................................... 548/183

[56] References Cited

FOREIGN PATENT DOCUMENTS 299620 1/1989 European Pat. Off. ............ 548/183

*Primary Examiner*—Robert Gerstl
*Attorney, Agent, or Firm*—Scully, Scott Murphy & Presser

[57] ABSTRACT

Novel benzoxazole derivatives of the formula:

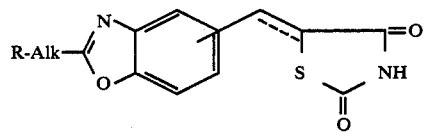

wherein R is a substituted or unsubstituted phenyl group, a substituted or unsubstituted naphthyl group, a substituted or unsubstituted cycloalkyl group or a substituted or unsubstituted heterocyclic group; Alk is single bond, a substituted or unsubstituted lower alkylene group, a lower alkenylene group or a lower alkynylene group; the group ⁄⋀ is a group of the formula: —CH$_2$— or —CH≡, and a pharmaceutically acceptable salt thereof are disclosed. Said derivative (I) and a salt thereof are useful as therapeutic agents for diabetes.

3 Claims, No Drawings

BENZOXAZOLE DERIVATIVES

This is a divisional of copending application Ser. No. 167,391, filed on Mar. 14, 1988 now U.S. Pat. No. 4,897,393.

This invention relates to a novel benzoxazole derivative, and processes for preparing same. More particularly, it relates to a benzoxazole derivative of the formula:

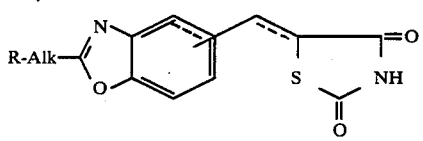

wherein R is a substituted or unsubstituted phenyl group, a substituted or unsubstituted naphthyl group, a substituted or unsubstituted cycloalkyl group or a substituted or unsubstituted heterocyclic group; Alk is single bond, a substituted or unsubstituted lower alkylene group, a lower alkenylene group or a lower alkynylene group; and the group is a group of the formula: —CH$_2$— or —CH=, or a pharmaceutically acceptable salt thereof.

A variety of biguanide derivatives and sulfonylurea derivatives have been so far used for treatment of diabetes. However, these anti-diabetic agents are still unsatisfactory in that the biguanide and sulfonylurea derivatives cause side effects such as lactic acidosis and severe hypoglycemia, respectively.

The novel benzoxazole derivative (I) of the present invention and a salt thereof are useful for therapeutic treatment of diabetes because they elevate insulin sensitivity and show potent hypoglycemic activity.

Examples of the benzoxazole derivative of the present invention are those of the formula (I) in which R is phenyl group, naphthyl group, cyclohexyl group, 1,3-thiazol-4-yl group, 1,3-oxazol-4-yl group, pyridyl group, benzoxazolyl group, thienyl group, quinolyl group or benzofuranyl group (these groups may optionally have a substituent or substituents selected from a (lower alkoxy)carbonyl group, a lower alkoxy group, a lower alkyl group, a trihalogeno-lower alkyl group, a lower alkylthio group, a lower alkylsulfinyl group, a lower alkylsulfonyl group, phenyl group, phenoxy group, a phenyl-lower alkoxy group, hydroxy group, a halogen atom, nitro group, amino group, a lower alkanoylamino group, a di(lower alkyl)amino group, a cycloalkyl group, pyrrolidino group, piperidino group, morphorino group and pyrrolyl group.); and Alk is single bond, a straight or branched lower alkylene group, a lower alkenylene group or a lower alkynylene group (said lower alkylene group may optionally be substituted with hydroxy group, oxygen atom, phenyl group or a cycloalkyl group.).

Among them, preferred examples of the benzoxazole derivative of the invention are those of the formula (I) in which R is ① a phenyl group which may optionally have 1 to 3 substituent(s) selected from the above mentioned groups; ② a naphthyl group which may optionally be substituted with a lower alkoxy group, a lower alkyl group, a halogen atom or nitro group; ③ a cyclohexyl or pyridyl group which may optionally be substituted with a lower alkyl group; ④ a 1,3-thiazol-4-yl or 1,3-oxazol-4-yl group which may optionally have 1 to 2 substituent(s) selected from a lower alkyl group, a lower alkylthio group, a cycloalkyl group and phenyl group; ⑤ a 1,3-benzoxazolyl group which may optionally be substituted with phenyl group; ⑥ thienyl group; ⑦ quinolyl group; or ⑧ benzofuranyl group.

More preferred examples of the compound of the invention are those of the formula (I) in which R is ① a phenyl group which may optionally have 1 to 3 substituent(s) selected from a lower alkoxy group, a lower alkyl group, a trihalogenolower alkyl group, a lower alkylthio group, a lower alkylsulfinyl group, a lower alkylsulfonyl group, phenyl group, a halogen atom, nitro group, pyrrolidino group, piperidino group, morphorino group, pyrrolyl group and a di(lower alkyl)amino group; ② a naphthyl group which may optionally be substituted with a lower alkoxy group, a lower alkyl group, a halogen atom or nitro group; ③ a pyridyl group which may optionally be substituted with a lower alkyl group; or ④ a 1,3-thiazol-4-yl or 1,3-oxazol-4-yl group which may optionally have 1 to 2 substituent(s) selected from a lower alkyl group, a lower alkylthio group, a cycloalkyl group and phenyl group.

Other preferred examples of the benzoxazole derivative of the invention are those of the formula (I) in which Alk is a straight or branched lower alkylene group and/or 2,4-dioxothiazolidin-5-yl(or ylidene)-methyl group is bound to the benzoxazole ring at the 5- or 6-position thereof, especially at the 5-position thereof.

In the above-mentioned examples of the benzoxazole derivative (I), the lower alkoxy group, the lower alkyl group, the lower alkanoyl group, the cycloalkyl group, the lower alkylene group, the lower alkenylene group and the lower alkynylene group include an alkoxy group of one to six carbon atoms, an alkyl group of one to six carbon atoms, an alkanoyl group of two to six carbon atoms, a cycloalkyl group of three to nine carbon atoms, an alkylene group of one to four carbon atoms, an alkenylene group of two to four carbon atoms and an alkynylene group of two to four carbon atoms, respectively. Preferred examples of these group are an alkyl group of one to four carbon atoms, an alkenyl, alkynyl or alkanoyl group of two to five carbon atoms, and a cycloalkyl group of four to seven carbon atoms.

On the other hand, the benzoxazole derivatives (I) of the present invention in which the 2,4-dioxothiazolidine binds to the benzoxazole ring via methylene group (i.e., the compound in which the group ⋀ is methylene group) may exist in the form of two optically active isomers due to the asymmetric carbon atom thereof. On the other hand, the benzoxazole derivative (I) of the present invention in which the 2,4-dioxothiazolidine binds to benzoxazole ring via a group of the formula: —CH= (i.e., the compound in which the group ⋀ is —CH=) may exist in the form of the two geometrical isomers. The present invention includes within its scope either one of these optical or geometrical isomers and a mixture thereof.

According to the present invention, the compound (I) can be prepared by the step of:

(1) condensing a compound of the formula:

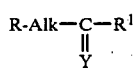

wherein $R^1$ is hydroxy group, a lower alkoxy group or a reactive residue, Y is oxygen atom or imino group, and R and Alk are the same as defined above, or a salt thereof with a dioxothiazolidine compound of the formula:

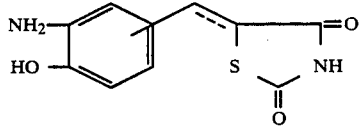

wherein the symbol is the same as defined above, or a salt thereof, (2) dehydrating an amide of the formula:

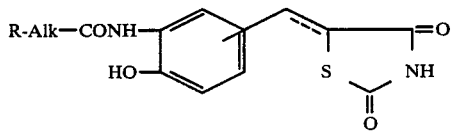

wherein the symbols are the same as defined above, or a salt thereof, or (3) dehydrogenating an azomethine compound of the formula:

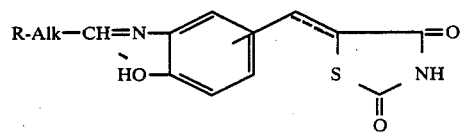

wherein the symbols are the same as defined above, or a salt thereof.

Among the compound (I) of the invention, an olefinic compound of the formula:

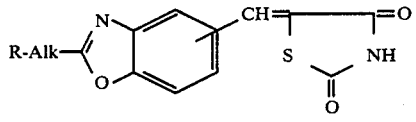

wherein the symbols are the same as defined above, may also be prepared by reacting an aldehyde compound of the formula:

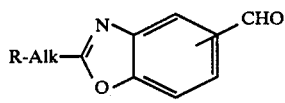

wherein the symbols are the same as defined above, or a salt thereof with 2,4-dioxothiazolidine or a salt thereof.

On the other hand, the compound of the formula:

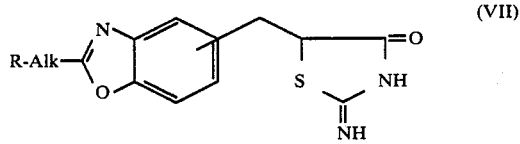

wherein the symbols are the same as defined above, may be prepared by hydrolysis of an imino compound of the formula:

(VII)

wherein the symbols are the same as defined above, or a salt thereof or reduction of the compound (I-b) or a salt thereof.

The starting compound (II) in which Y is oxygen atom, and the starting compound (III) to (V) and (VII), compound (I-b) and 2,4-dioxothiazolidine, may, if required, be used for the above reactions in the form of a mineral acid salt (e.g., hydrochloride), an alkali metal salt, an alkaline earth metal salt. The starting compound (II) in which Y is imino group and the starting compound (VI) may, if required, be used for the above reaction in the form of a salt with a mineral acid (e.g., hydrochloric acid).

When the group Y is oxygen atom, the condensation of the starting compound (II) or a salt thereof and the dioxothiazolidine compound (III) or a salt thereof can be conducted in the presence or absence of a condensing agent. Preferred examples of the reactive residue ($R^1$) include halogen atoms such as chlorine or bromine atoms. Trimethylsilyl polyphosphate, ethyl polyphosphate and the like are preferably used as the condensing agent. If required, the reaction may be carried out in an inert solvent such as dichlorobenzene, dichloromethane, tetrahydrofuran, benzene or toluene. On the other hand, when the group Y is imino group, the condensation of the starting compound (II) or a salt thereof and the compound (III) can be conducted in a solvent. Dioxane, tetrahydrofuran, ethanol or methanol are suitable as the solvent. Either one of these reactions may be carried out at 40° to 260° C.

The dehydration of the amide (IV) or a salt thereof can be conducted in the presence or absence of a dehydrating agent or an acid. It is preferred to carry out the reaction in an inert solvent such as those mentioned above; but, if the reaction is carried out in the absence of the dehydrating agent or an acid, it is not always necessary to use a solvent. Preferred examples of the dehydrating agent and acid include phosphoryl chloride, thionyl chloride, trimethylsilyl polyphosphate, ethyl polyphosphate, p-toluenesulfonic acid and the like. It is preferred to carry out the reaction at 50° to 250° C.

The dehydrogenation of the azomethine compound (V) or a salt thereof can be conducted in the presence of a dehydrogenating agent. Examples of such dehydrogenating agent include lead tetraacetate, nickel peroxide and the like. It is preferred to carry out the reaction at 0° to 100° C. in a solvent such as dioxane, tetrahydrofuran, benzene, toluene, water, ethyl acetate, acetic acid, pyridine and the mixture thereof.

The reaction of aldehyde compound (VI) or a salt thereof and 2,4-dioxothiazolidine or a salt thereof can be conducted in the presence or absence of a base. Piperidine, pyridine, a tri(lower alkyl)amine, sodium hydride, sodium methylate, sodium ethylate, lithium diisopropyl amide, etc., can be used as a base. The solvent which is used in the condensation of the compound (II) in which Y is imino group can be used in this reaction. It is preferred to carry it out at 0° to 150° C.

Hydrolysis of the imino compound (VII) or a salt thereof can be conducted in an inert solvent according to a conventional manner. For example, said hydrolysis is preferably carried out by treating the compound (VII) with an acid such as hydrochloric acid, hydrobromic acid, hydroiodic acid, p-toluenesulfonic acid, trifluoroacetic acid, methanesulfonic acid and the like. It is also preferred to carry it out at 50° to 150° C. On the other hand, reduction of olefinic compound (I-b) or a salt thereof can be conducted in the presence of a catalyst in hydrogen atmosphere. Palladium carbon, palladium, platinum oxide or Raney nickel can be used as a catalyst. It is preferred to carry it out at 10° to 80° C. In these hydrolysis and reduction, dioxane, tetrahydrofuran, ethanol, methanol, ethylene glycol monomethyl ether, acetic acid and the mixture thereof are suitable as the solvent.

Concomitantly, the benzoxazole derivative (I) of the invention in which Alk is a lower alkylene group substituted with oxo group may be converted into the corresponding benzoxazole derivative (I) in which Alk is a hydroxy-lower alkylene group. This conversion is carried out by reduction of the former derivative with a reducing agent such as sodium borohydride at 0° to 100° C. in an inert solvent such as methanol, ethanol, tetrahydrofuran and the mixture thereof. On the other hand, the benzoxazole derivative (I) in which R is a lower alkylsulfinyl- or lower alkylsulfonylphenyl group may be obtained by oxidation of the benzoxazole derivative (I) in which R is a lower alkylthiophenyl group. Said oxidation is preferably carried out by treatment with an oxidative agent such as m-chloroperbenzoic acid, perbenzoic acid or peracetic acid at −70° to 100° C. in an inert solvent such as lower alkanol, methylene chloride, chloroform, tetrahydrofuran, dioxane, water and the mixture thereof. Alternatively, the benzoxazole derivative (I) in which R is a hydroxyphenyl group may be obtained by debenzylation of the benzoxazole derivative (I) in which R is benzyloxyphenyl group. Said debenzylation is preferably carried out by treatment with an acid such as hydrochloric acid or hydrobromic acid at 0° to 100° C. in an inert solvent such as acetic acid.

The benzoxazole derivative (I) of the present invention and a salt thereof exhibit potent hypoglycemic activity and are useful for treatment and/or prophylaxis of diabetes, especially for the treatment of patients with non-insulin dependent diabetes. Such therapeutic effect of the compound (I) is based on the elevation of insulin sensitivity in cells and, unlike the known anti-diabetic agents, said compound is advantageous in that it can be used as an anti-diabetic agent without affecting patients of normal blood glucose level. Moreover, the toxicity of the benzoxazole derivative (I) of the present invention is low. For example, when 5-[(2,4-dioxothiazolidin-5-yl)methyl]-2-[(2-phenylthiazol-4-yl)methyl]benzoxazole at a dose of 100 mg/kg (CMC suspension) was orally administered to mice, no mice died during a 72 hour-observation period.

The benzoxazole derivative (I) can be used for pharmaceutical use either in the free form or in the form of a salt. Suitable salts of the compound (I) for pharmaceutical use include, for example, pharmaceutically acceptable salts such as an alkali metal salt (e.g., sodium salt, potassium salt), an alkaline earth metal salt (e.g., calcium salt, magnesium salt), and acid addition salts (hydrochloride or sulfate). Such salt may be obtained by treating the compound (I) with a stoichiometrically equimoler amount of the acid or base according to a conventional manner.

The compound (I) and a salt thereof may be administered either orally or parenterally and may also be used in the form of a pharmaceutical preparation containing the same compound in admixture with pharmaceutical excipients suitable for oral or parenteral administration. The pharmaceutical preparations may be in solid form such as tablets, capsules or suppositories or in liquid form such as solutions, suspensions or emulsions. Moreover, when administered parenterally, the phamaceutical preparation may be used in the form of injections.

The dose of the compound (I) or a salt thereof may vary depending on the age, condition and body weight of patients, the kind and severity of diseases to be treated and administration route, etc, but may usually be about 0.005 to about 100 mg/kg, preferably about 0.01 to about 10 mg/kg, per day.

All of the starting compounds (III) to (VII) of the invention are novel. Among them, the dioxothiazolidine compound (III) in which the group ⌒ is methylene group can be prepared by hydrolyzing a compound of the formula:

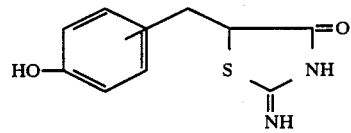

and then nitrating the product with conc. nitric acid, followed by reduction with a reducing agent such as sodium hypophosphite in the presence of a catalyst such as palladium-carbon at 0° to 100° C. On the other hand, the dioxothiazolidine compound (III) in which the group ⌒ is a group of the formula: —CH= can be prepared by condensing 4-hydroxy-3-nitrobenzaldehyde or 3-hydroxy-4-nitrobenzaldehyde with 2,4-dioxothiazolidine in the presence of a base (e.g., piperidine), and then treating the product with a reducing agent (e.g., sodium hypophosphite) in the presence of a catalyst (e.g., palladium carbon). The amide (IV) can be prepared by condensing the dioxothiazolidine compound (III) and the compound (II) under a mild condition, e.g., in the presence of a condensing agent such as dicyclohexylcarbodiimide. The azomethine compound (V) can be prepared by condensing the compound of the formula:

R—Alk—CHO wherein the symbols are the same as defined above, or a salt thereof with the dioxothiazolidine compound (III) in the presence or absence of a catalyst (e.g., hydrochloric acid). Aldehyde compound (VI) can be prepared by dehydrating the compound of the formula:

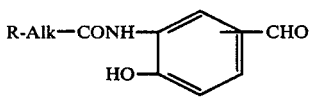

wherein the symbols are the same as defined above, or a salt thereof according to the same condition of the dehydration of the compound (IV). Further, the imino compound (VI) or a salt thereof can be prepared by diazotizing the aniline compound of the formula:

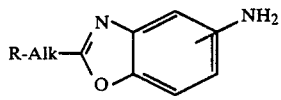

(VII)

wherein the symbols are the same as defined above, or a salt thereof in the presence of hydrogen halide, reacting the product with methyl acrylate in the presence of a copper catalyst (e.g., copper(I) oxide), and then reacting the product with thiourea in the presence of a base such as sodium acetate.

Experiment

Genetically obese and diabetic mice, KK-A$^y$ (Tokyo Laboratory Animals Science Corp., Tokyo, Japan; 1.5 to 11 months old), were used. Mice were divided into groups of 4 mice with roughly equal means in blood glucose level and body weight after prefeeding powdered chow (CE-2, Clea Japan Inc., Tokyo, Japan). Mice were fed ad libilum for 5 days the powdered chow containing 0.5 mg % of test compound After 5 days, blood was collected from the tail tip. Blood glucose was enzymatically determined. Hypoglycemic activity of test compound was calculated as follows;

$$\left(1 - \frac{\text{blood glucose level of the medicated group}}{\text{blood glucose level of the non-medicated group}}\right) \times 100$$

The results are shown in Table 1.

TABLE 1

| Test compounds | Hypoglycemic activity |
|---|---|
| 5-[(2,4-dioxothiazolidin-5-yl)methyl]-2-[(2-phenylthiazol-4-yl)methyl]benzoxazole | 63% |
| 5-[(2,4-dioxothiazolidin-5-yl)methyl]-2-[(2-phenyloxazol-4-yl)methyl]benzoxazole | 52% |
| 5-[(2,4-dioxothiazolidin-5-yl)methyl]-2-[(5-methyl-2-cyclohexyloxazol-4-yl)methyl]benzoxazole | 49% |
| 5-[(2,4-dioxothiazolidin-5-yl)methyl]-2-[(5-methyl-2-phenyloxazol-4 yl)methyl]benzoxazole | 58% |

EXAMPLE 1

(1) A mixture of 1.76 g of sodium nitrite in 5 ml of water is added dropwise under ice-cooling to a mixture of 4.87 g of 5-amino-2-phenylbenzoxazole, 6 ml of conc. hydrochloric acid and 50 ml of acetone. The mixture is stirred at the same temperature for 10 minutes, and then 12.1 g of methyl acrylate are added thereto. 150 mg of copper(I) oxide are added gradually to the mixture at 40° C. After nitrogen gas evolution ceases, the mixture is kept at 35° C. for 20 minutes. Water is added thereto, and the aqueous mixture is extracted with ethyl acetate. The extract is washed with water, dried and evaporated to remove the solvent. The residue is purified by silica gel column chromatograghy (solvent; chloroform), whereby 5.13 g of methyl 3-(2-phenylbenzoxazol-5-yl)-2-chloropropionate are obtained as pale brown oil.

IR $\nu_{max}^{neat}$ (cm$^{-1}$): 1740

(2) A mixture of 5.13 g of the product obtained above, 2.30 g of thiourea, 1.50 g of sodium acetate and 35 ml of ethylene glycol monomethyl ether is heated at 100° C. for 8 hours. The solvent is distilled off, and water and n-hexane are added to the residue. The precipitated crystals are collected by filtration, washed, and dried, whereby 4.35 g of 5-[(2-imino-4-oxothiazolidin-5-yl)methyl]-2-phenylbenzoxazole are obtained as colorless powder.

M.p. 281° to 283° C. (decomp.)

(3) 3.18 g of the product obtained above are dissolved in 50 ml of ethylene glycol monomethyl ether, and 2.05 g of toluenesulfonic acid monohydrate and 6 ml of water are added thereto. After the mixture is refluxed for 1 hour and 45 minutes, the solvent is distilled off. Water is added to the residue, and the solution is extracted with ethyl acetate. The extract is washed, dried, and evaporated to remove the solvent. The residue is purified by silica gel column chromatography (solvent; chloroform:methanol=20:1), whereby 1.83 g of 5-[(2,4-dioxothiazolidin-5-yl)methyl]-2-phenylbenzoxazole are obtained.

M.p. 192° to 194° C.
Mass(m/e): 324(M$^+$)
IR $\nu_{max}^{Nujol}$ (cm$^{-1}$): 3180,1745,1680

EXAMPLES 2 to 4

The corresponding starting compounds are treated in the same manner as described in Example 1 to give the compounds shown in Table 2.

TABLE 2

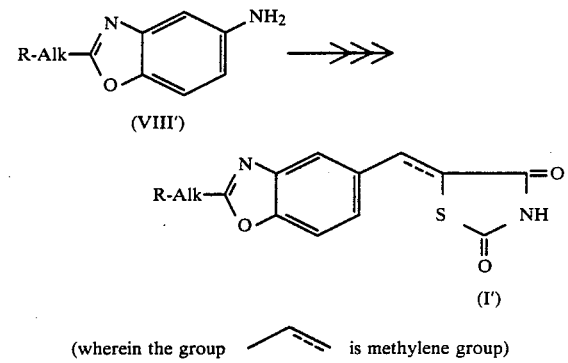

(wherein the group ⌒ is methylene group)

| Ex. No. | Compound(I') R-Alk- | Properties |
|---|---|---|
| 2 | cyclohexyl-CH(CH$_3$)- | M.p. 107 to 110° C. Mass(m/e): 344(M$^+$) IR*: 1770, 1685 |
| 3 | 4-Cl-phenyl- | M.p. 209 to 212° C. Mass(m/e): 358,360(M$^+$) IR*: 1760, 1740, 1700, 1685 |

TABLE 2-continued

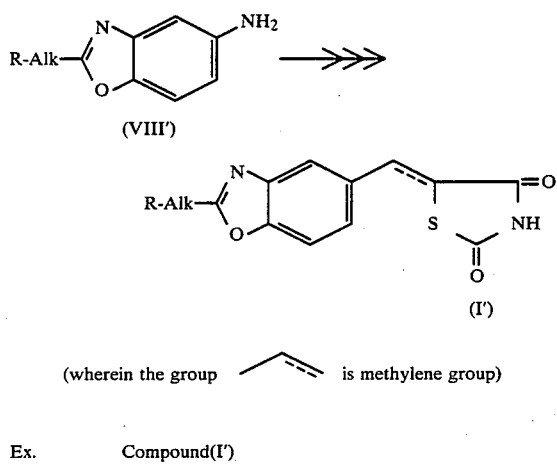

(wherein the group ⌢⌣ is methylene group)

| Ex. No. | Compound(I') R-Alk- | Properties |
|---|---|---|
| 4 | [phenyl]—CH=CH— | M.p. 219 to 222° C. Mass(m/e): 350(M+) IR*: 1740, 1680 |

*: IR $\nu_{max}^{Nujol}$(cm$^{-1}$) (same in the following Examples)

EXAMPLE 5

(1) A solution containing 2.38 g of 2-phenyl-4-thiazoleacetyl chloride in 10 ml of tetrahydrofuran is added dropwise at 0° C. to the mixture of 3.10 g of 5-(3-amino-4-hydroxybenzyl)-2,4-dioxothiazolidine, 3.63 g of N,N-dimethylaniline, 25 ml of tetrahydrofuran and 5 ml of dimethylformamide, and the mixture is stirred at room temperature for 20 minutes. After the reaction, the mixture is poured into water, and extracted with ethyl acetate. The extract is washed, dried and evaporated to remove the solvent. The residue is crystallized with ethyl acetate, whereby 3.35 g of N-[5-(2,4-dioxothiazolidin-5-yl)methyl-2-hydroxyphenyl]-2-phenylthiazole-4-acetamide are obtained.

Yield 76%

M.p. 227° to 229° C. (decomp.)

Mass(m/e): 439(M+), 202

IR $\nu_{max}^{Nujol}$ (cm$^{-1}$): 1740, 1690, 1670

(2) 1.5 g of the product obtained above are added to a trimethylsilyl polyphosphate solution prepared from 3.2 g of phosphorus pentaoxide, 6.6 ml of hexamethyldisiloxane, and 12.5 ml of 1,2-dichloroethane. The mixture is heated at 100° C. for 30 minutes. The reaction mixture is poured into ice-water, and extracted with ethyl acetate. The extract is dried, and evaporated to remove the solvent. The residue is recrystallized from methanol, whereby 880 mg of 5-[(2,4-dioxothiazolidin-5-yl)methyl]-2-[(2-phenyl-1,3-thiazol-4-yl)methyl]benzoxazole are obtained.

Yield 61%

M.p. 86° to 89° C.

Mass(m/e): 421(M+), 305

IR $\nu_{max}^{Nujol}$ (cm$^{-1}$): 1750, 1690

EXAMPLE 6

(1) A mixture of 2.03 g of 2-phenyl-4-oxazoleacetic acid, 2.38 g of 5-(3-amino-4-hydroxybenzyl)-2,4-dioxothiazolidine, 2.06 g of dicyclohexylcarbodiimide, 2 ml of dimethylformamide and 20 ml of tetrahydrofuran is stirred at room temperature for 18 hours. After the reaction, insoluble materials are filtered off. The filtrate is poured into ice-water, and the solution is extracted with ethyl acetate. The extract is washed with water, dried and evaporated to remove the solvent. The residue is purified by silica gel column chromatography (solvent; chloroform:methanol=10:1), whereby 2.83 g of N-[5-(2,4-dioxothiazolidin-5-yl)methyl-2-hydroxyphenyl]-2-phenyloxazole-4-acetamide are obtained.

Yield 67%

M.p. 197.5° to 199.5° C.

Mass(m/e): 423(M+), 186

IR $\nu_{max}^{Nujol}$ (cm$^{-1}$): 1740, 1690, 1670

(2) 635 mg of the product obtained above are heated at 230° C. for 40 minutes. After cooling, the reaction product is purified by silica gel column chromatography (solvent; chloroform:methanol=10:1), and recrystallized from acetonitrile, whereby 383 mg of 5-[(2,4-dioxothiazolidin-5-yl)methyl]-2-[(2-phenyl-1,3-oxazol-4-yl)methyl]benzoxazole are obtained.

Yield 63%

M.p. 174° to 177.5° C.

Mass(m/e): 405(M+), 289

IR $\nu_{max}^{Nujol}$ (cm$^{-1}$): 1730, 1710

EXAMPLES 7 to 30

The corresponding starting compounds are treated in the same manner as described in Example 5-(1) and (2) or 6-(1) and (2) to give the compounds shown in Table 3.

TABLE 3

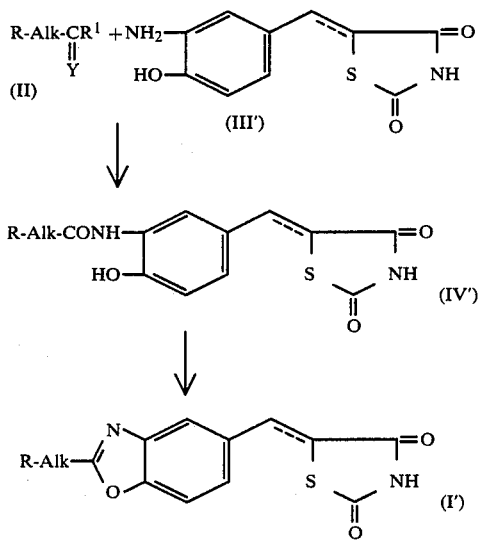

(wherein Y is oxygen atom, R¹ is hydrogen atom, and the group ⌒ is methylene group)

| Ex. No. | Compound(I') R-Alk- | Properties |
|---|---|---|
| 7 | CH₃-C(=N-)-S- attached to -CH(Et)- | M.p. 167.5 to 168° C.<br>Mass(m/e): 359($M^+$)<br>IR*: 1740, 1700 |
| 8 | Ph-C(=N-)-S-CH₂- (thiazoline) | M.p. 239 to 242° C.<br>Mass(m/e): 407($M^+$), 291<br>IR*: 1740, 1690 |
| 9 | C₆H₅-CH₂- | M.p. 158 to 159° C.<br>Mass(m/e): 338($M^+$), 222<br>IR*: 1750, 1690 |
| 10 | 2-pyridyl-CH₂- | M.p. 177 to 180° C.<br>Mass(m/e): 339($M^+$), 223<br>IR*: 1730, 1700 |
| 11 | cyclohexyl-CH₂- | M.p. 86 to 89° C.<br>Mass(m/e): 344($M^+$), 262, 228<br>IR*: 1750, 1690 |
| 12 | 2-MeO-C₆H₄-CH₂- | M.p. 79.5 to 81.0° C.<br>Mass(m/e): 368($M^+$)<br>IR*: 1760, 1745, 1700 |
| 13 | 4-(CH₃)₂N-C₆H₄-CH₂- | M.p. 217 to 218° C.<br>Mass(m/e): 381($M^+$)<br>IR*: 1745, 1680 |

TABLE 3-continued

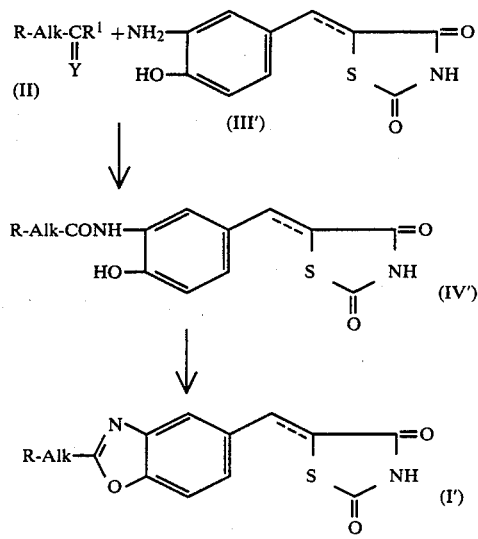

(wherein Y is oxygen atom, $R^1$ is hydrogen atom, and the group ⌒ is methylene group)

| Ex. No. | Compound(I') R-Alk- | Properties |
|---|---|---|
| 14 | $(C_2H_5)_2N$—⟨C₆H₄⟩—$CH_2$— | M.p. 162 to 163° C.<br>Mass(m/e): 409(M⁺)<br>IR*: 1760, 1700 |
| 15 | (pyrrolidinyl)—⟨C₆H₄⟩—$CH_2$ | M.p. 229 to 232° C.<br>Mass(m/e): 407(M⁺)<br>IR*: 1750, 1690 |
| 16 | (piperidinyl)—⟨C₆H₄⟩—$CH_2$— | M.p. 205 to 208° C.<br>Mass(m/e): 421(M⁺)<br>IR*: 1750, 1690 |
| 17 | (morpholinyl)—⟨C₆H₄⟩—$CH_2$— | M.p. 213 to 215° C.<br>Mass(m/e): 423(M⁺)<br>IR*: 1760, 1740, 1700 |
| 18 | $(CH_3)_2N$—⟨C₆H₄⟩—$CH_2$— | M.p. 161 to 171° C.<br>Mass(m/e): 381(M⁺)<br>IR*: 1745, 1705 |
| 19 | (piperidinyl)—⟨C₆H₄⟩—$CH_2$— | pale yellow powder<br>Mass(m/e): 421(M⁺)<br>IR*: 1750, 1700 |
| 20 | (naphthyl with $OCH_3$)—$CH_2$— | M.p. 183 to 186° C.<br>Mass(m/e): 418(M⁺)<br>IR*: 1750, 1700 |
| 21 | (naphthyl with $CH_3$)—$CH_2$— | M.p. 201 to 202° C.<br>Mass(m/e): 402(M⁺)<br>IR*: 1735, 1700 |

TABLE 3-continued

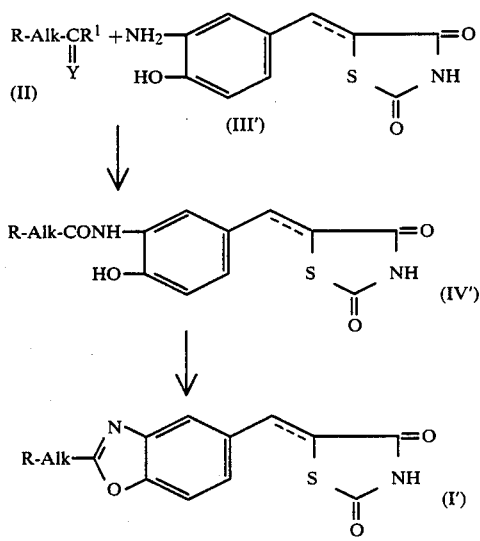

(wherein Y is oxygen atom, R¹ is hydrogen atom, and the group  is methylene group)

| Ex. No. | Compound(I') R-Alk- | Properties |
|---|---|---|
| 22 | CH₃OCO—⟨C₆H₄⟩—CH₂— | M.p. 153 to 155° C. Mass(m/e): 396(M⁺) IR*: 1740, 1725, 1705 |
| 23 | C₂H₅—⟨pyridin-2-yl⟩—CH₂— (5-ethyl) | M.p. 165 to 167° C. Mass(m/e): 367(M⁺) IR*: 1770, 1740, 1700 |
| 24 | C₆H₅—C≡C— | M.p. 180 to 183° C. Mass(m/e): 348(M⁺) IR*: 2220, 1750, 1690 |
| 25 | Cl—⟨C₆H₄⟩—(CH₂)₃— | M.p. 129 to 132° C. Mass(m/e): 402, 400(M⁺) IR*: 1755, 1730, 1690 |
| 26 | Cl—⟨C₆H₄⟩—C(CH₃)₂— | M.p. 154 to 156° C. Mass(m/e): 402, 400(M⁺) IR*: 1755, 1730, 1690, 1670 |
| 27 | (1-NO₂-naphth-2-yl)—CH₂— | M.p. 183 to 184° C. Mass(m/e): 433(M⁺) IR*: 1745, 1705 |
| 28 | (benzofuran-2-yl)—CH₂— | M.p. 158 to 160° C. Mass(m/e): 378(M⁺) IR*: 1750, 1730, 1690 |
| 29 | (quinolin-6-yl)—CH₂— | M.p. 251.5 to 254° C. Mass(m/e): 389(M⁺) IR*: 1740, 1695 |

TABLE 3-continued

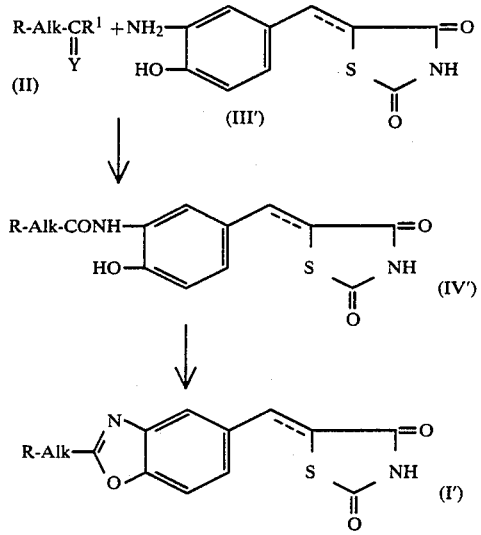

(wherein Y is oxygen atom, R¹ is hydrogen atom, and the group ⁀ is methylene group)

| Ex. No. | Compound(I')<br>R-Alk- | Properties |
|---|---|---|
| 30 | (2-phenyl-benzoxazol-5-yl)-CH₂— | M.p. 208 to 210° C.<br>Mass(m/e): 455(M+)<br>IR*: 1740, 1700 |

EXAMPLE 31

A mixture of 4.0 g of phosphorus pentaoxide, 10 ml of hexamethyldisiloxane, and 20 ml of 1,2-dichlorobenzene is refluxed for 5 minutes to give a trimethylsilyl polyphosphate solution. Then, 1.52 g of 2-phenyl-5-methyl-4-oxazoleacetic acid and 2.17 of 5-(3-amino-4-hydroxybenzyl)-2,4-dioxothiazolidine are added thereto, and the mixture is heated at 150° C. for 2 hours. The reaction mixture is poured into ice-water, and extracted with ethyl acetate. The extract is washed with water, dried and evaporated to remove the solvent. The residue is purified by silica gel column chromatography (solvent; chloroform:methanol=100:1), and recrystallized from a mixture of ethyl acetate and n-hexane, whereby 1.99 g of 5-[(2,4-dioxothiazolidin-5-yl)methyl]-2-[(2-phenyl-5-methyl-1,3-oxazol-4-yl)methyl]benzoxazole are obtained.

Yield 68%

M.p. 175° to 178° C.

Mass(m/e): 419(M+), 348, 303

IR $\nu_{max}^{Nujol}$ (cm⁻¹): 1745, 1700, 1640

EXAMPLES 32 to 72

The corresponding starting compounds are treated in the same manner as described in Example 31 to give the compounds shown in Table 4.

TABLE 4

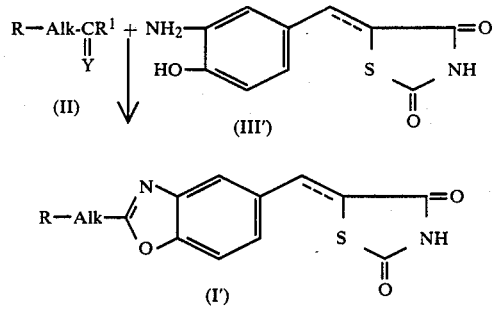

| Ex. No. | Compound(I')<br>R—Alk- | Properties |
|---|---|---|

(part 1) (wherein Y is oxygen atom, R¹ is hydrogen atom, and the group ⁀ is methylene group)

TABLE 4-continued

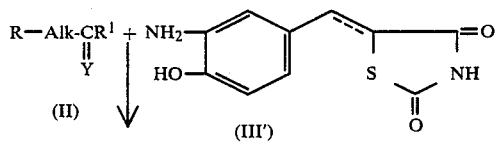

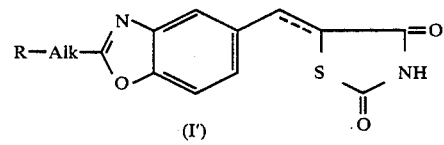

| Ex. No. | Compound(I') R—Alk- | Properties |
|---|---|---|
| 32 | (cyclohexyl)CH-thiazole-N= with ethyl | M.p. 86 to 89° C.<br>Mass(m/e): 427(M+), 372, 359<br>IR*: 1770, 1690 |
| 33 | (cyclohexyl)CH-oxazole with CH3 and ethyl | M.p. 146 to 148° C.<br>Mass(m/e): 425(M+)<br>IR*: 1760, 1680 |
| 34 | phenyl-thiazole substituent | M.p. 288 to 289° C.<br>Mass(m/e): 480(M+), 458<br>IR*: 1665, 1565 |
| 35 | CH3S-thiazole with ethyl | M.p. 174.5 to 176° C.<br>Mass(m/e): 391(M+)<br>IR*: 1740, 1700 |
| 36 | CH3-oxazole with CH3 and ethyl | M.p. 177 to 179° C.<br>Mass(m/e): 357(M+)<br>IR*: 1770, 1740, 1700 |
| 37 | F-C6H4-CH2— | M.p. 183 to 186° C.<br>Mass(m/e): 356(M+)<br>IR*: 1740, 1690 |
| 38 | CH3O-C6H4-CH2— | M.p. 143 to 146° C.<br>Mass(m/e): 368(M+)<br>IR*: 1760, 1740, 1710 |
| 39 | CH3-C6H4-CH2— | M.p. 180 to 183° C.<br>Mass(m/e): 352(M+)<br>IR*: 1760, 1740, 1710 |

TABLE 4-continued
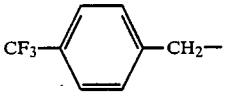
| Ex. No. | Compound(I') R—Alk- | Properties |
|---|---|---|
| 40 | 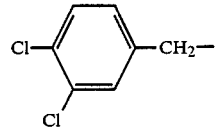 4-CF₃-C₆H₄-CH₂- | M.p. 173 to 174°·C. Mass(m/e): 406(M⁺) IR*: 1750, 1730, 1690 |
| 41 | 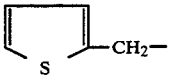 3,4-Cl₂-C₆H₃-CH₂- | M.p. 156.5 to 159.5° C. Mass(m/e): 406, 408, 410(M⁺) IR*: 1740, 1700 |
| 42 | 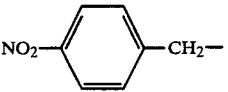 2-thienyl-CH₂- | M.p. 139 to 141° C. Mass(m/e): 344(M⁺) IR*: 1750, 1690 |
| 43 | 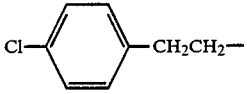 4-NO₂-C₆H₄-CH₂- | M.p. 118 to 121° C. Mass(m/e): 383(M⁺) IR*: 1720, 1700 |
| 44 | 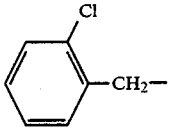 4-Cl-C₆H₄-CH₂CH₂- | M.p. 75 to 78° C. Mass(m/e): 386, 388(M⁺) IR*: 1750, 1690 |
| 45 | 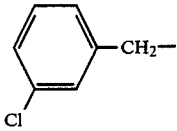 2-Cl-C₆H₄-CH₂- | M.p. 139 to 141° C. Mass(m/e): 372, 374(M⁺) IR*: 1740, 1700 |
| 46 | 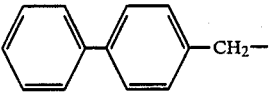 3-Cl-C₆H₄-CH₂- | M.p. 170.5 to 172° C. Mass(m/e): 372, 374(M⁺) IR*: 1745, 1700 |
| 47 | 4-biphenyl-CH₂- | M.p. 194 to 197° C. Mass(m/e): 414(M⁺) IR*: 1745, 1680 |
| 48 | 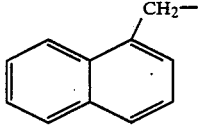 1-naphthyl-CH₂- | M.p. 150 to 152.5° C. Mass(m/e): 388(M⁺) IR*: 1745, 1690 |

TABLE 4-continued

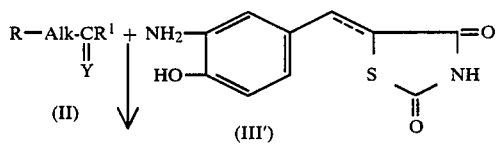

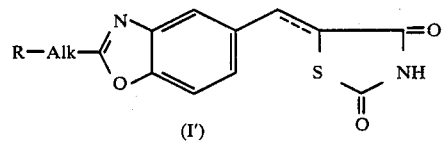

| Ex. No. | Compound(I') R—Alk- | Properties |
|---|---|---|
| 49 |  2-naphthyl-CH$_2$— | M.p. 208.5 to 210.5° C.<br>Mass(m/e): 388(M$^+$)<br>IR*: 1745, 1680 |
| 50 |  4-Cl-C$_6$H$_4$—CH(CH$_3$)— | colorless powder<br>Mass(m/e): 388, 386(M$^+$)<br>IR*: 1750, 1690 |
| 51 |  cyclohexyl(phenyl)CH— | colorless powder<br>Mass(m/e): 420(M$^+$)<br>IR*: 1750, 1695 |
| 52 |  (C$_6$H$_5$)$_2$CH— | colorless powder<br>Mass(m/e): 414(M$^+$)<br>IR*: 1750, 1690 |
| 53 |  (C$_6$H$_5$)$_2$CH—CH$_2$— | M.p. 175 to 178° C.<br>Mass(m/e): 428(M$^+$)<br>IR*: 1740, 1690 |
| 54 |  4-Cl-C$_6$H$_4$—C(CH$_3$)$_2$—CH$_2$— | colorless powder<br>Mass(m/e): 416, 414(M$^+$)<br>IR*: 1750, 1695 |
| 55 |  3-CH$_3$O-C$_6$H$_4$—CH$_2$— | M.p. 137 to 140° C.<br>Mass(m/e): 368(M$^+$)<br>IR*: 1745, 1705 |
| 56 |  4-C$_2$H$_5$O-C$_6$H$_4$—CH$_2$— | M.p. 165 to 168° C.<br>Mass(m/e): 382(M$^+$)<br>IR*: 1745, 1705 |

TABLE 4-continued

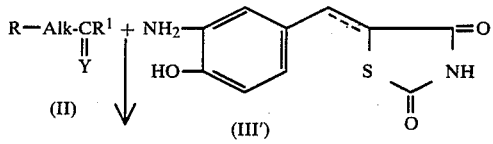

| Ex. No. | Compound(I') R—Alk- | Properties |
|---|---|---|
| 57 | 4-C₄H₉O-C₆H₄-CH₂— | M.p. 155 to 157° C. Mass(m/e): 410(M⁺) IR*: 1750, 1690 |
| 58 | C₆H₅-O-C₆H₄-CH₂— (4-phenoxyphenyl)methyl | M.p. 122 to 123° C. Mass(m/e): 430(M⁺) IR*: 1745, 1690 |
| 59 | C₆H₅-CH₂O-C₆H₄-CH₂— (4-benzyloxyphenyl)methyl | M.p. 138 to 141° C. Mass(m/e): 444(M⁺) IR*: 1745, 1685 |
| 60 | 3,4-(CH₃O)₂-C₆H₃-CH₂— | M.p. 163 to 166° C. Mass(m/e): 398(M⁺) IR*: 1745, 1700 |
| 61 | 3,4,5-(CH₃O)₃-C₆H₂-CH₂— | M.p. 190 to 193° C. Mass(m/e): 428(M⁺) IR*: 1750, 1700 |
| 62 | 4-(pyrrol-1-yl)-C₆H₄-CH₂— | M.p. 183 to 185° C. Mass(m/e): 403(M⁺) IR*: 1750, 1700 |
| 63 | 2-(N(C₂H₅)₂)-C₆H₄-CH₂— | foam Mass(m/e): 409(M⁺) IR*: 1750, 1700 |
| 64 | 6-methoxy-naphth-2-yl-CH₂— | M.p. 203 to 205.5° C. Mass(m/e): 418(M⁺) IR*: 1750, 1690 |
| 65 | 6-methyl-naphth-2-yl-CH₂— | M.p. 225.5 to 227.5° C. Mass(m/e): 402(M⁺) IR*: 1745, 1685 |

TABLE 4-continued

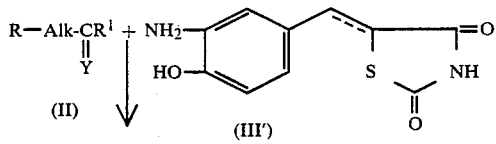

(II)     (III')

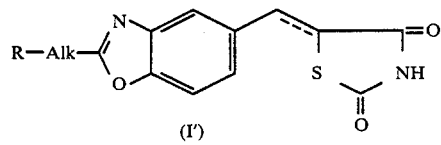

(I')

| Ex. No. | Compound(I') R—Alk- | Properties |
|---|---|---|
| 66 | 6-chloro-2-naphthyl-CH$_2$— | M.p. 214 to 216° C. Mass(m/e): 424, 422(M$^+$) IR*: 1750, 1680 |
| 67 | CH$_3$S—C$_6$H$_4$—CH$_2$— | M.p. 144 to 147° C. Mass(m/e): 384(M$^+$) IR*: 1740, 1700 |
| 68 | (CH$_3$)$_3$C—C$_6$H$_4$—CH$_2$— | M.p. 159 to 162° C. Mass(m/e): 394(M$^+$) IR*: 1760, 1740, 1700 |
| 69 | C$_6$H$_5$—CO— | M.p. 188 to 189° C. Mass(m/e): 352(M$^+$) IR*: 1740, 1710, 1680 |

(part 2) (wherein Y is oxygen atom, R$^1$ is hydrogen atom, and the group ⁀ is methine group)

| 70 | 2-phenyl-5-ethyl-4-methyloxazol-4-yl | M.p. 261.5 to 263° C. Mass(m/e): 417(M$^+$) IR*: 1740, 1720, 1700 |
| 71 | 2-phenyl-5-ethylthiazol-4-yl | M.p. 221 to 222.5° C. Mass(m/e): 419(M$^+$) IR*: 1740, 1705 |
| 72 | 4-Cl—C$_6$H$_4$—CH$_2$— | M.p. 218 to 219.5° C. Mass(m/e): 372, 370(M$^+$) IR*: 1735, 1705 | note
*: sodium salt

EXAMPLE 73

A mixture of 500 mg of 5-(3-amino-4-hydroxybenzyl)-2,4-dioxothiazolidine, 405 mg of 2-phenyl-4-formylthiazole and 30 ml of ethanol is refluxed for 20 minutes, and the solvent is distilled off. 840 mg of 4-(2,4-dioxothiazolidin-5-yl)methyl-2-[(phenylthiazol-4-yl)methylidene]aminophenol obtained as a crude product are dissolved in 40 ml of benzene, and 1.26 g of lead tetraacetate are added thereto. After the mixture is stirred at room temperature for 15 minutes, the solvent is distilled off. Ethyl acetate and water are added to the residue, and the ethyl acetate layer is washed with water, dried, and evaporated to remove the solvent. The residue is purified by silica gel column chromatography (solvent; chloroform:methanol=100:1), whereby 400 mg of 5-[(2,4-dioxothiazolidin-5-yl)methyl]-2-(2-phenyl-1,3-thiazol-4-yl)benzoxazole are obtained. The Mass and IR data of this product are identical with those of the product obtained in Example 8.

EXAMPLE 74

(1) 9.47 g of N-(5-amino-2-hydroxyphenyl)-2-(4-chlorophenyl)acetamide are treated in the same manner as described in Example 1-(1) to (3) to give 5.64 g of N-[5-(2,4-dioxothiazolidin-5-yl)methyl-2-hydroxyphenyl]-2-(4-chlorophenyl)acetamide as pale yellow powder.

M.p. 207° to 209° C.
Mass(m/e): 392, 390(M+)
IR $\nu_{max}^{Nujol}$ (cm$^{-1}$): 1750, 1720

(2) 5.64 g of the product obtained above are heated at 220° C. for 50 minutes. After cooling, the products are purified by silica gel column chromatography (solvent; chloroform:methanol=50:1), and recrystallized from ether, whereby 4.0 g of 5-[(2,4-dioxothiazolidin-5-yl)methyl]-2-(4-chlorobenzyl)benzoxazole are obtained.

M.p. 169.5° to 170.5° C.
Mass(m/e): 374, 372(M+)
IR $\nu_{max}^{Nujol}$ (cm$^{-1}$): 1750, 1690

EXAMPLE 75

N-(5-amino-2-hydroxyphenyl)-4-hydroxy-3,5-di(-tert.-butyl)benzamide is treated in the same manner as described in Example 74 to give 5-[(2,4-dioxothiazolidin-5-yl)methyl]-2-[4-hydroxy-3,5-di(tert.-butyl)-phenyl]benzoxazole.

M.p. 213° to 216° C.
Mass(m/e): 452(M+)
IR $\nu_{max}^{Nujol}$ (cm$^{-1}$): 1750, 1700

EXAMPLE 76

N-(4-amino-2-hydroxyphenyl)-2-(4-chlorophenyl)acetamide is treated in the same manner as described in Example 74 to give 6-[(2,4-dioxothiazolidin-5-yl)methyl]-2-[4-chlorobenzyl]benzoxazole.

M.p. 219.5° to 220.5° C.
Mass(m/e): 374, 372(M+)
IR $\nu_{max}^{Nujol}$ (cm$^{-1}$): 1745, 1695

EXAMPLE 77

3.48 g of 5-[(2,4-dioxothiazolidin-5-yl)methyl]-2-(4-nitrobenzyl)benzoxazole are dissolved in a mixture of 70 ml of tetrahydrofuran and 70 ml of methanol, and 2.5 g of 10% palladium-carbon are added thereto. The mixture is subjected to catalytic hydrogenation in hydrogen gas atmosphere under atmospheric pressure. Insoluble materials are filtered off, and the filtrate is condensed. The residue is purified by silica gel column chromatography (solvent; chloroform:methanol=20:1) and recrystallized from ethyl acetate, whereby 1.86 g of 5-[(2,4-dioxothiazolidin-5-yl)methyl]-2-(4-aminobenzyl)-benzoxazole are obtained.

M.p 180° to 183° C.
Mass(m/e): 353(M+)
IR $\nu_{max}^{Nujol}$ (cm$^{-1}$): 1735, 1700

EXAMPLE 78

A mixture of 0.99 g of 5-[(2,4-dioxothiazolidin-5-yl)methyl]-2-(4-aminobenzyl)benzoxazole, 2 ml of acetic anhydride and 10 ml of pyridine is stirred at room temperature overnight. 10% Hydrochloric acid is added thereto, and the solution is extracted with ethyl acetate. The extract is washed with water, dried and evaporated to remove the solvent. The residue is recrystallized from ethyl acetate, whereby 0.56 g of 5-[(2,4-dioxothiazolidin-5-yl)methyl]-2-(4-acetamidobenzyl)benzoxazole is obtained.

M.p. 233° to 236° C.
Mass(m/e): 395(M+)
IR $\nu_{max}^{Nujol}$ (cm$^{-1}$): 1745, 1690

EXAMPLE 79

A mixture of 1.0 g of 5-[(2,4-dioxothiazolidin-5-yl)methyl]-2-(4-methylthiobenzyl)benzoxazole, 0.58 g of 80% m-chloroperbenzoic acid and 25 ml of methylene chloride is stirred at room temperature for 10 minutes. The solvent is distilled off, and ethyl acetate is added to the residue. The ethyl acetate solution is washed, dried and evaporated to remove the solvent. The residue is purified by silica gel column chromatography (solvent; chloroform:methanol=20:1), whereby 0.67 g of 5-[(2,4-dioxothiazolidin-5-yl)methyl]-2-(4-methylsulfinylbenzyl)benzoxazole are obtained as colorless foam.

Yield 64%
Mass(m/e): 400(M+)
IR $\nu_{max}^{Nujol}$ (cm$^{-1}$): 1750, 1690

EXAMPLE 80

A mixture of 1.2 g of 5-[(2,4-dioxothiazolidin-5-yl)methyl]-2-(4-methylthiobenzyl)benzoxazole, 2.1 g of 80% m-chloroperbenzoic acid and 30 ml of methylene chloride is stirred at room temperature for 20 minutes. The reaction mixture is treated in the same manner as described in Example 79, and recrystallized from a mixture of tetrahydrofuran and n-hexane, whereby 1.2 g of 5-[(2,4-dioxothiazolidin-5-yl)methyl]-2-(4-methylsulfonylbenzyl)benzoxazole are obtained as colorless powder.

Yield 69%
M.p. 168° to 169° C.

EXAMPLE 81

1.3 g of 5-[(2,4-dioxothiazolidin-5-yl)methyl)-2-(benzoyl)benzoxazole are dissolved in a mixture of 30 ml of methanol and 6 ml of tetrahydrofuran, and 0.14 g of sodium borohydride is added thereto. After the mixture is stirred at room temperature for 5 minutes, water is added thereto. The solution is extracted with ethyl acetate, and the extract is evaporated to remove the solvent. The residue is crystallized with ether, whereby 0.64 g of 5-[(2,4-dioxothiazolidin-5-yl)methyl]-2-(α-hydroxybenzyl)benzoxazole is obtained as colorless crystal.

M.p. 210° to 212° C. (decomp.)

EXAMPLE 82

A mixture of 0.95 g of 5-[(2,4-dioxothiazolidin-5-yl)methyl)-2-(4-benzyloxybenzyl)benzoxazole, 10 ml of a 25% hydrogen bromide solution in acetic acid and 10 ml of acetic acid is stirred at room temperature overnight. Ethyl acetate and water are added to the reaction mixture. The ethyl acetate layer is washed with water, dried and evaporated to remove the solvent. The residue is crystallized with n-hexane, and recrystallized from a mixture of ethyl acetate and n-hexane, whereby 0.42 g of 5-[(2,4-dioxothiazolidin-5-yl)methyl]-2-(4-hydroxybenzyl)benzoxazole is obtained as colorless needles.

Yield 55%
M.p. 201° to 204° C.
Mass(m/e): 354(M+)
IR $\nu_{max}^{Nujol}$ (cm$^{-1}$): 3340, 1730, 1690

EXAMPLE 83

(1) 5-(3-amino-4-hydroxybenzyl)-2,4-dioxothiazolidine and 4-(N,N-dimethylamino)phenylacetyl chloride, prepared from 4-(N,N-dimethylamino)phenylacetic acid and oxalyl chloride, are treated in the same manner as described in Example 5-(1) to give N-[5-(2,4-dioxothiazolidin-5-yl)methyl-2-hydroxyphenyl]-2-(4-dimethylaminophenyl)acetamide.
M.p. 215.5° to 217.5° C.

(2) A mixture of 6.0 g of the product obtained above, 0.3 g of p-toluenesulfonic acid monohydrate and 35 ml of diethylaniline is refluxed for 1.5 hours. After cooling, the precipitated crystals are collected by filtration. The crystals are washed and recrystallized from a mixture of tetrahydrofuran and methanol, whereby 4.9 g of 5-[(2,4-dioxothiazolidin-5-yl)methyl]-2-(4-dimethylaminobenzyl)benzoxazole are obtained.
Yield 78%
M.p. 217° to 218° C.

(Preparation of Starting Compounds)

Preparation 1

(1) A solution of 6.16 g of 2-amino-4-nitrophenol and 4.77 g of benzaldehyde in ethanol is refluxed. The reaction solution is condensed and cooled. The crystalline precipitates are collected by filtration to give 2-benzylideneamino-4-nitrophenol. 15.5 g of lead tetraacetate are added to a benzene suspension of the product obtained above, and the mixture is stirred. After the reaction, insoluble materials are filtered off. The filtrate is washed, and condensed. The residue is purified by silica gel column chromatography and recrystallized from ethanol, whereby 5.08 g of 5-nitro-2-phenylbenzoxazole are obtained.
M.p. 169° to 171.5° C.

(2) 3 g of 10% palladium-carbon are added to an acetic acid solution of 8.85 g of the product obtained above, and the mixture is subjected to catalytic hydrogenation in hydrogen gas atmosphere. Insoluble materials are filtered off, and the filtrate is condensed. The residue is recrystallized from a mixture of chloroform and n-hexane, whereby 7.02 g of 5-amino-2-phenylbenzoxazole are obtained.
M.p. 150.5° to 153° C.

Preparation 2

(1) 16.0 g of (1-methylcyclohexyl)carbonyl chloride are added dropwise to a tetrahydrofuran solution of 14.7 g of 2-amino-4-nitrophenol and 12.1 g of N,N-dimethylaniline under ice-cooling, and the mixture is stirred at room temperature. 10% Hydrochloric acid is added to the reaction mixture, and the crystals are collected by filtration. The crystals are added to 260 ml of thionyl chloride, then the mixture is refluxed. Thionyl chloride which remains unreacted is distilled off, and the residue is purified by silica gel column chromatography, whereby 21.7 g of 2-(1-methylcyclohexyl)-5-nitrobenzoxazole are obtained.
M.p. 57° to 59° C.

(2) The product obtained above is treated in the same manner as described in Preparation 1-(2) to give 5-amino-2-(1-methylcyclohexyl)benzoxazole as a colorless oil.
Mass(m/e): 230(M+)

Preparations 3 and 4

The corresponding starting compounds are treated in the same manner as described in Preparation 1 or 2 to give the compounds shown in Table 5.

TABLE 5

R-Alk—[benzoxazole]—NH$_2$ (VIII')

| Pr. No. | Compound(VIII') R-Alk- | Properties |
|---|---|---|
| 3 | Cl—C$_6$H$_4$— | M.p. 177 to 180° C. |
| 4 | C$_6$H$_5$—CH=CH— | M.p. 148 to 150.5° C. |

Preparation 5

(1) A mixture of 8.55 g of 4-chlorophenylacetic acid and 5 ml of thionyl chloride is heated. After the reaction, thionyl chloride is distilled off. The residue is added to a tetrahydrofuran solution of 7.70 g of 2-amino-4-nitrophenol and 6.65 g of N,N-dimethylaniline, and the mixture is stirred at room temperature. The solvent is distilled off, and diluted hydrochloric acid is added to the residue. Then, the crystals are collected by filtration, whereby 14.2 g of N-(5-nitro-2-hydroxyphenyl)-2-(4-chlorophenyl)acetamide are obtained.
M.p. 250° to 252° C. (decomp.)

(2) 13.93 g of the product obtained above are added to a ethanol-ethyl acetate suspension of tin(II) chloride, and the mixture is heated. After the reaction, the solvent is distilled off, and the residue is neutralized with sodium hydroxide. The mixture is extracted with ethyl acetate. The extract is evaporated to remove the solvent, and the residue is recrystallized from ethyl acetate, whereby 9.86 g of N-(5-amino-2-hydroxyphenyl)-2-(4-chlorophenyl)acetamide are obtained.
M.p. 164° to 167° C.

Preparation 6

4-hydroxy-3,5-di(tert.-butyl)benzoic acid and 2-amino-4-nitrophenol are treated in the same manner as described in Preparation 5-(1) and Preparation 1-(2) to give N-(5-amino-2-hydroxyphenyl)-4-hydroxy-3,5-di(tert.-butyl)benzamide are obtained.
M.p. 222° to 225° C. (decomp.)

Preparation 7

(1) 4-aminophenol is treated in the same manner as described in Example 1-(1) to (3) to give 5-(4-hydroxybenzyl)-2,4-dioxothiazolidine.
M.p. 157° to 158.5° C.

(2) 5.19 g of the product obtained above are added to 50 ml of 70% nitric acid under ice-cooling, and the mixture is stirred for 5 minutes. The reaction mixture is poured into ice-water, and extracted with ethyl acetate.

The extract is washed with water, dried, and evaporated to remove the solvent. The residue is recrystallized from a mixture of ethyl acetate and n-hexane, whereby 4.85 g of 5-(4-hydroxy-3-nitrobenzyl)-2,4-dioxothiazolidine are obtained.

Yield 78%

M.p. 141° to 143.5° C.

(3) 10% palladium-carbon, 4M-aqueous sodium hypophosphite solution and water are added to a dimethylformamide solution of 1.0 g of the product obtained above, and the mixture is stirred at room temperature. After the reaction, insoluble materials are filtered off. Water is added to the filtrate, and the solution is extracted with ethyl acetate. The extract is evaporated to remove the solvent, and the residue is recrystallized from isopropylalcohol, whereby 755 mg of 5-(3-amino-4-hydroxybenzyl)-2,4-dioxothiazolidine are obtained.

M.p. 215° to 217.5° C. (decomp.)

Preparation 8

(1) A mixture of 18.0 g of 4-hydroxy-3-nitrobenzaldehyde, 12.74 g of 2,4-dioxothiazolidine, 2.2 ml of piperidine and 180 ml of dioxane is refluxed for 13 hours. After cooling, 100 ml of water and 10 ml of 10% hydrochloric acid are added thereto. The crystalline precipitates are collected by filtration, dried, and recrystallized from a mixture of tetrahydrofuran and n-hexane, whereby 14.8 g of 5-(4-hydroxy-3-nitrobenzylidene)-2,4-dioxothiazolidine are obtained.

Yield 52%

M.p. 256.5° to 258° C.

(2) 12.85 g of the product obtained above are treated in the same manner as described in Preparation 7-(3) and the filtrate is poured into water. The crystalline precipitates are collected by filtration, whereby 10.86 g of 5-(3-amino-4-hydroxybenzylidene)-2,4-dioxothiazolidine are obtained.

Yield 95%

M.p. 260.5° to 261.5° C.

Preparation 9

(1) A solution of 13.3 g of L-4-hydroxy-3-nitrophenylalanine and 35 g of potassium bromide in 170 ml of an aqueous 3N-sulfuric acid is cooled in ice-bath. Then, a solution of 4.95 g of sodium nitrite in 10 m of water is added dropwise to the mixture for 30 minutes. After the reaction at the same temperature for 10 minutes, the mixture is extracted with ethyl acetate. The ethyl acetate layer is washed with water, dried and evaporated to remove the solvent, whereby 15.2 g of 2-bromo-3-(4-hydroxy-3-nitrophenyl)propionic acid are obtained as brown solid.

(2) A mixture of 15.1 g of the product obtained above, 6.14 g of thiourea, 5.51 g of sodium acetate and 150 ml of ethanol is refluxed for 3 hours. The solvent is distilled off, and water is added to the residue. The precipitates are collected by filtration, washed, and dried, whereby 12.2 g of 5-(4-hydroxy-3-nitrobenzyl)-2-imino-4-oxo-thiazolidine are obtained as yellow powder.

M.p. 221° to 223° C. (decomp.)

(3) A mixture of 12.1 g of the product obtained above, 15.6 ml of conc. hydrochloric acid, 125 ml of ethylene glycol monomethyl ether and 12.5 ml of water is refluxed for 4 hours. The reaction mixture is condensed and the residue is extracted with ethyl acetate. The ethyl acetate layer is washed with water, dried, and evaporated to remove the solvent. The residue is recrystallized from a mixture of ethyl acetate and n-hexane, whereby 10 4 g of 5-(4-hydroxy-3-nitrobenzyl)-2,4-dioxothiazolidine are obtained as yellow powder.

M.p. 141° to 143.5° C.

(4) 10.3 g of the product obtained above are dissolved in 170 ml of a mixture of tetrahydrofuran and methanol, and 2.5 g of 10% palladium-carbon are added thereto. The mixture is subjected to catalytic hydrogenation at atmospheric pressure. The catalyst is filtered off, and filtrate is condensed. Isopropyl alcohol is added to the residue, whereby 8.77 g of 5-(3-amino-4-hydroxybenzyl)-2,4-dioxothiazolidine are obtained as pale yellow powder.

M.p. 215° to 217.5° C.

What is claimed is:

1. A compound of the formula:

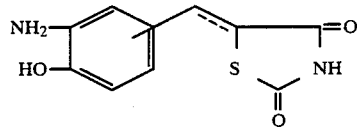

wherein the group ⌒ is a group of the formula: —CH$_2$— or —CH═, or a salt thereof.

2. The compound according to claim 1 which has the formula:

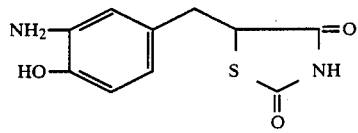

3. The compound according to claim 1 which has the formula:

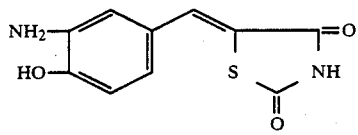

* * * * *